(12) United States Patent
Hsu et al.

(10) Patent No.: US 12,236,814 B2
(45) Date of Patent: Feb. 25, 2025

(54) DISPLAY METHOD AND DISPLAY SYSTEM FOR ANTI-DIZZINESS REFERENCE IMAGE

(71) Applicant: INDUSTRIAL TECHNOLOGY RESEARCH INSTITUTE, Hsinchu (TW)

(72) Inventors: Ya-Rou Hsu, Tongxiao Township (TW); Chien-Ju Lee, Taoyuan (TW); Hong-Ming Dai, Tainan (TW); Yu-Hsiang Tsai, Zhubei (TW); Chia-Hsun Tu, Taipei (TW); Kuan-Ting Chen, Douliu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 18/202,432

(22) Filed: May 26, 2023

(65) Prior Publication Data
US 2023/0386371 A1 Nov. 30, 2023

Related U.S. Application Data

(60) Provisional application No. 63/345,917, filed on May 26, 2022.

(30) Foreign Application Priority Data

Apr. 27, 2023 (TW) .................................. 112115718

(51) Int. Cl.
*G09G 3/00* (2006.01)
*G06F 3/01* (2006.01)

(52) U.S. Cl.
CPC ............. *G09G 3/001* (2013.01); *G06F 3/013* (2013.01); *G09G 2320/0626* (2013.01);
(Continued)

(58) Field of Classification Search
CPC ........... G09G 3/001; G09G 2320/0626; G09G 2320/08; G09G 2340/045; G06F 3/013
See application file for complete search history.

(56) References Cited

U.S. PATENT DOCUMENTS

| | | | |
|---|---|---|---|
| 4,926,346 A | 5/1990 | Yokoyama | |
| 8,594,381 B2 * | 11/2013 | Fedorovskaya | G02B 27/017 382/107 |

(Continued)

FOREIGN PATENT DOCUMENTS

| | | |
|---|---|---|
| CN | 106601198 A | 4/2017 |
| CN | 110843673 A | 2/2020 |

(Continued)

OTHER PUBLICATIONS

Taiwanese Office Action and Search Report for Taiwanese Application No. 112115718, dated Apr. 9, 2024.

*Primary Examiner* — Gene W Lee
(74) *Attorney, Agent, or Firm* — Birch, Stewart, Kolasch & Birch, LLP

(57) ABSTRACT

A display method and a display system for an anti-dizziness reference image are provided. The display system includes a display, a range extraction unit, an information analyzing unit, an object analyzing unit and an image setting unit. The display is used to display the anti-dizziness reference image. The range extraction unit is used to obtain a gaze background range of a user. The image setting unit is used to set an image hue, an image lightness, an image brightness, an image content or an ambient lighting display content of the anti-dizziness reference image according to a background hue information, a background lightness information, a background brightness information, or a road information of the gaze background range; or set an image ratio between the anti-dizziness reference image and a display area of the (Continued)

display according to an object distance or an object area of the watched object.

20 Claims, 13 Drawing Sheets

(52) U.S. Cl.
CPC . *G09G 2320/0666* (2013.01); *G09G 2320/08* (2013.01); *G09G 2340/045* (2013.01); *G09G 2354/00* (2013.01); *G09G 2380/10* (2013.01)

(56) References Cited

U.S. PATENT DOCUMENTS

| | | | | |
|---|---|---|---|---|
| 8,619,005 B2* | 12/2013 | Cok | .................. | G02B 27/0172 345/178 |
| 8,692,845 B2* | 4/2014 | Fedorovskaya | ...... | G02B 27/017 345/619 |
| 8,831,278 B2* | 9/2014 | Fedorovskaya | ...... | H04N 13/144 382/103 |
| 9,996,754 B2 | 8/2018 | Brauer | | |
| 10,297,060 B2* | 5/2019 | Park | ....................... | G09G 3/003 |
| 10,481,686 B2* | 11/2019 | Komatsu | ................ | G06F 3/013 |
| 10,578,877 B1 | 3/2020 | Lin et al. | | |
| 10,684,479 B2* | 6/2020 | Chen | .................. | G02B 27/0172 |
| 10,849,496 B2* | 12/2020 | Murakami | ............... | A61B 5/18 |
| 10,901,213 B2* | 1/2021 | Yamaguchi | ........... | G02B 27/017 |
| 10,957,262 B2* | 3/2021 | Chen | ....................... | G09G 5/02 |
| 10,989,927 B2* | 4/2021 | Lanman | ............. | G02B 27/0093 |
| 11,069,321 B2* | 7/2021 | Chen | ..................... | G06T 7/0002 |
| 11,269,579 B2* | 3/2022 | Fujii | ..................... | G06F 3/1446 |
| 11,328,494 B2* | 5/2022 | Adachi | ..................... | G06T 5/73 |
| 11,366,318 B2* | 6/2022 | Jeon | ..................... | H04N 13/398 |
| 11,907,417 B2* | 2/2024 | Haine | ..................... | G06F 3/012 |
| 2012/0182206 A1* | 7/2012 | Cok | ..................... | G02B 27/017 345/8 |
| 2019/0187790 A1* | 6/2019 | Woo | ..................... | G06F 3/013 |
| 2020/0090626 A1* | 3/2020 | Chen | ..................... | G09G 5/10 |
| 2020/0158944 A1* | 5/2020 | Wang | .................. | G02B 6/0073 |
| 2020/0357355 A1 | 11/2020 | Ma et al. | | |
| 2021/0233315 A1* | 7/2021 | Jung | ..................... | H04B 1/385 |
| 2022/0176996 A1* | 6/2022 | Park | ..................... | B60K 35/28 |
| 2023/0001790 A1* | 1/2023 | Kusafuka | ............. | H04N 13/317 |

FOREIGN PATENT DOCUMENTS

| | | |
|---|---|---|
| CN | 113168822 A | 7/2021 |
| CN | 113190199 A | 7/2021 |
| CN | 114415436 A | 4/2022 |
| TW | 201322732 A1 | 6/2013 |
| TW | 202026711 A | 7/2020 |
| TW | 1717824 B | 2/2021 |
| TW | I751932 B | 1/2022 |

* cited by examiner

DISPLAY METHOD AND DISPLAY SYSTEM FOR ANTI-DIZZINESS REFERENCE IMAGE

This application claims the benefit of U.S. Provisional application Ser. No. 63/345,917 filed May 26, 2022 and Taiwan application Serial No. 112115718, filed Apr. 27, 2023, the disclosure of which are incorporated by reference herein.

TECHNICAL FIELD

The disclosure relates to a display method and a display system for an anti-dizziness reference image.

BACKGROUND

It is inevitable that there will be shaking when the vehicle is driving. In order to reduce the user's dizziness, an anti-dizziness reference image can be provided to balance the user's vision and vestibular perception to improve the ride comfort.

However, if the anti-dizziness reference image is too eye-catching, it is easy to over-attract the user's attention and interfere with the user's vision. Moreover, the anti-dizziness reference image may also block the scenery outside the window and reduce the visual experience. In order to improve the user's comfort, researchers are working on improving the display technology of anti-dizziness reference image to overcome the current problems.

SUMMARY

The disclosure is related to a display method and a display system for an anti-dizziness reference image.

According to one embodiment, a display method for an anti-dizziness reference image is provided. The display method includes the following steps. A gaze background range of a user is obtained. A background hue information, a background lightness information, a background brightness information or a road information of the gaze background range is obtained. An object distance or an object area of a watched object in the gaze background range is obtained. An image hue, an image lightness, an image brightness, an image content or an ambient lighting display content of the anti-dizziness reference image is set according to the background hue information, the background lightness information, the background brightness information or the road information of the gaze background range; or an image proportion of the anti-dizziness reference image to a display area of the display unit is set according to the object distance or the object area of the watched object. A display unit displays the anti-dizziness reference image.

According to another embodiment, a display system for an anti-dizziness reference image is provided. The display system includes a display unit, a range extracting unit, an information analyzing unit, an object analyzing unit and an image setting unit. The display unit is used to display the anti-dizziness reference image. The range extracting unit is used to obtain a gaze background range of a user. The information analyzing unit is used to obtain a background hue information, a background lightness information, a background brightness information or a road information of the gaze background range. The object analyzing unit is used to obtain an object distance or an object area of a watched object in the gaze background range. The image setting unit is used to set an image hue, an image lightness, an image brightness, an image content or an ambient lighting display content of the anti-dizziness reference image according to the background hue information, the background lightness information, the background brightness information or the road information of the gaze background range; or used to set an image proportion of the anti-dizziness reference image to a display area of the display unit according to the object distance or the object area of the watched object.

Figure 3:
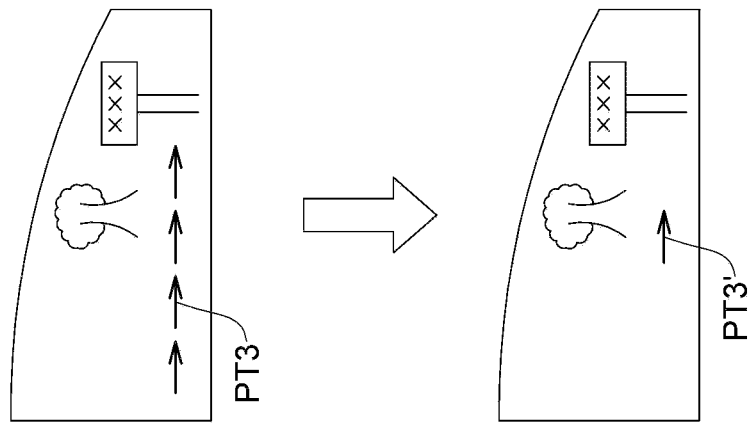
FIG. 3 illustrates an example of the modification of an anti-dizziness reference image.

In the following detailed description, for purposes of explanation, numerous details are set forth in order to provide a thorough understanding of the disclosed embodiments. It will be apparent, however, that one or more embodiments may be practiced without these details. In other instances, well-known structures and devices are schematically shown in order to simplify the drawing.

DETAILED DESCRIPTION

Figure 1:
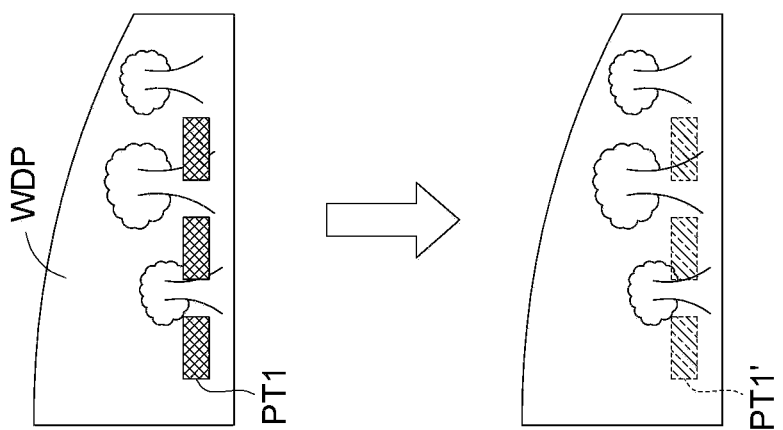
FIG. 1 illustrates an example of the modification of an anti-dizziness reference image.

Please refer to FIG. 1, which illustrates an example of the modification of an anti-dizziness reference image PT1. The anti-dizziness reference image PT1 is, for example, displayed on a transparent display unit WDP of a window. The anti-dizziness reference image PT1 is, for example, an explanatory text, a slogan, a trademark, an explanatory pattern or a meaningless pattern. The anti-dizziness reference image PT1 can balance the user's vision and vestibular perception to avoid the dizziness of the user.

However, as shown in FIG. 1, when a hue, a lightness (value) or a brightness of the anti-dizziness reference image PT1 obviously exceeds that of the trees in the background, the user visual is disturbed. In addition, the anti-dizziness reference image PT1 may also obscure the trees in the background and affect the user's visual experience.

In order to improve user comfort, the anti-dizziness reference image PT1 is modified to be the anti-dizziness reference image PT1' in this embodiment. The anti-dizziness reference image PT1' is provided by setting an image hue, an image lightness (value), an image brightness or an image content thereof, so that the viewing comfort of the anti-dizziness reference image PT1' can be improved.

Figure 2:
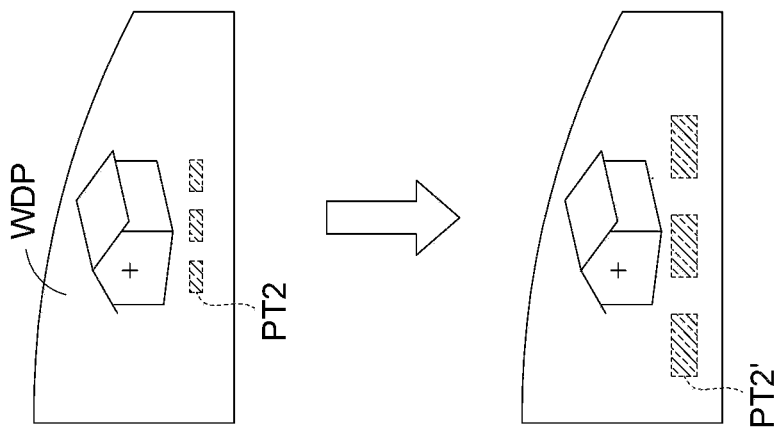
FIG. 2 illustrates an example of the modification of an anti-dizziness reference image.

Please refer to FIG. 2, which illustrates an example of the modification of an anti-dizziness reference image PT2. The anti-dizziness reference image PT2' may be too large and too eye-catching, so that the visual experience is reduced.

In order to improve user comfort, the anti-dizziness reference image PT2 is modified to be the anti-dizziness reference image PT2' in this embodiment. The anti-dizziness reference image PT2' is provided by setting an image proportion thereof, so that the viewing comfort is improved.

Please refer to FIG. 3, which illustrates an example of the modification of an anti-dizziness reference image PT3. The anti-dizziness reference image PT3 may be too complex, so that the user's vision is interfered and the visual experience is reduced.

In order to improve visual comfort, the anti-dizziness reference image PT3 is modified to be the anti-dizziness reference image PT3'. The anti-dizziness reference image PT3' is provided by setting an image content thereof, so that the viewing comfort is improved.

Figure 4:
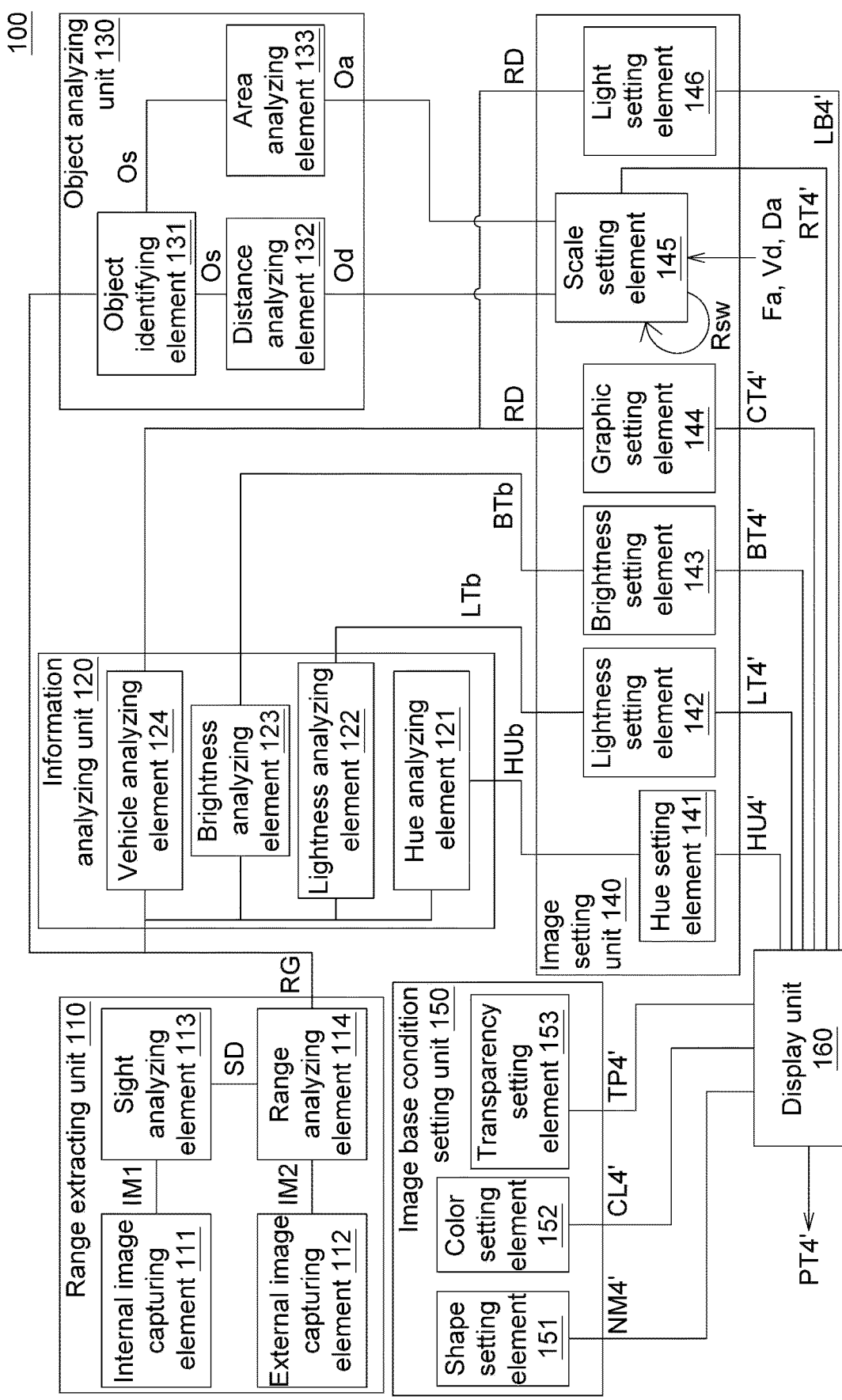
FIG. 4 shows a block diagram of a display system according to an embodiment.

Please refer to FIG. 4, which shows a block diagram of a display system 100 according to an embodiment. The display system 100 includes a range extracting unit 110, an information analyzing unit 120, an object analyzing unit 130, an image setting unit 140, an image base condition setting unit 150 and a display unit 160. The display unit 160 is used to display an anti-dizziness reference image PT4'. For example, the display unit 160 includes a transparent display on a window of a vehicle, a meter display panel, an entertainment device, a surrounding display around the seat, etc. The range extracting unit 110 includes, for example, an internal image capturing element 111, an external image capturing element 112, a sight analyzing element 113 and a range analyzing element 114. The internal image capturing element 111 is used to capture a vehicle interior image IM1, and the external image capturing element 112 is used to capture a vehicle external image IM2. The internal image capturing element 111 and the external image capturing element 112 are, for example, cameras, infrared sensors, lidar devices or other suitable devices. The sight analyzing element 113 is used to analyze a line-of-sight SD of the user U1 (shown in FIG. 7) according to the vehicle interior image IM1. The range analyzing element 114 obtains a gaze background range RG according to the line-of-sight SD and the vehicle external image IM2.

The information analyzing unit 120, the object analyzing unit 130, the image setting unit 140 and the image base condition setting unit 150 are used to execute various image analysis/processing procedures. In this embodiment, the display system 100 sets an image hue HU4', an image lightness (value) LT4', an image brightness BT4', an image content CT4', an ambient lighting display content LB4', an image proportion RT4' of the anti-dizziness reference image PT4' to a display area of the display unit 160, a number of lines NM4', an image saturation CL4' or an image transparency TP4', etc. The operation of the elements is described in detail below with a flow chart.

Figure 5:
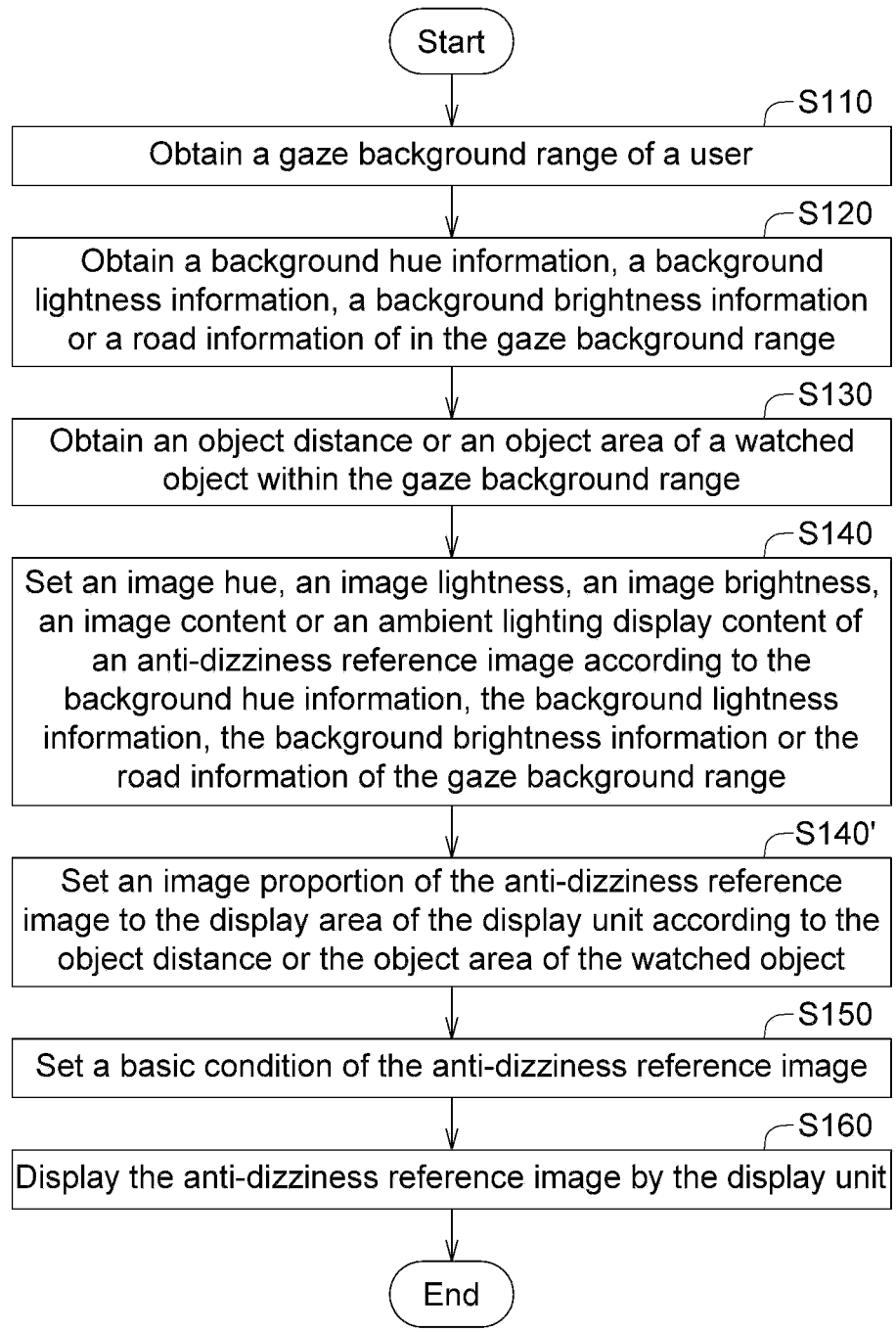
FIG. 5 shows a flow chart of a display method of the anti-dizziness reference image according to an embodiment.

Please refer to FIG. 5, which shows a flow chart of a display method of the anti-dizziness reference image PT4' according to an embodiment. In step S110, as shown in FIG. 4, the gaze background range RG of the user U1 (shown in FIG. 7) is obtained by the range extracting unit 110.

Figure 6:
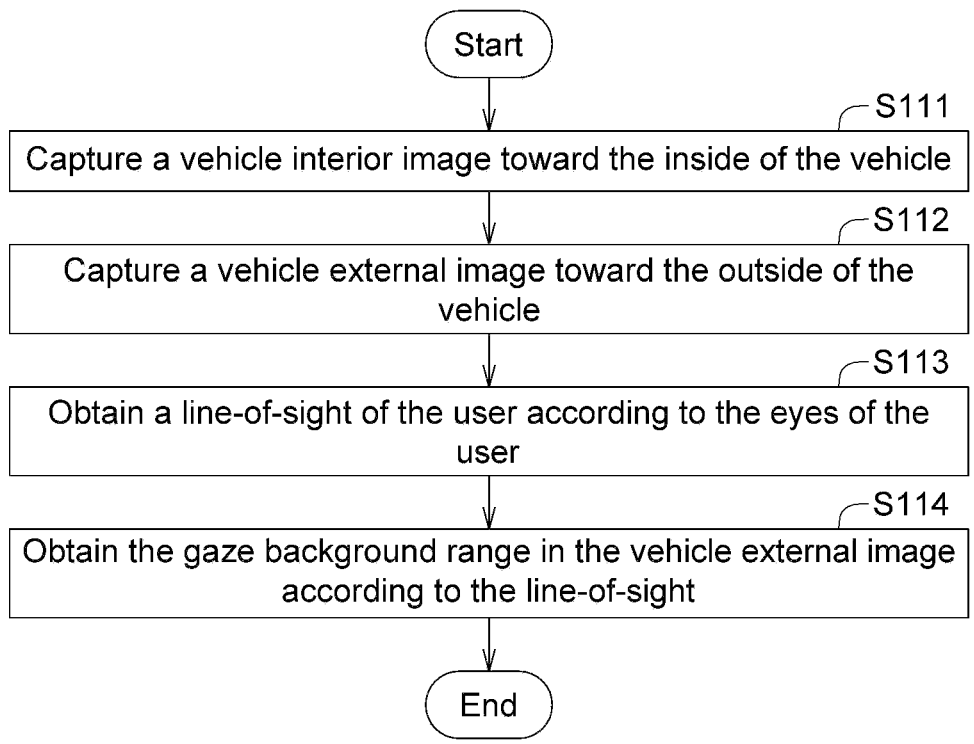
FIG. 6 shows the detailed flowchart of the step S110.
Figure 7:
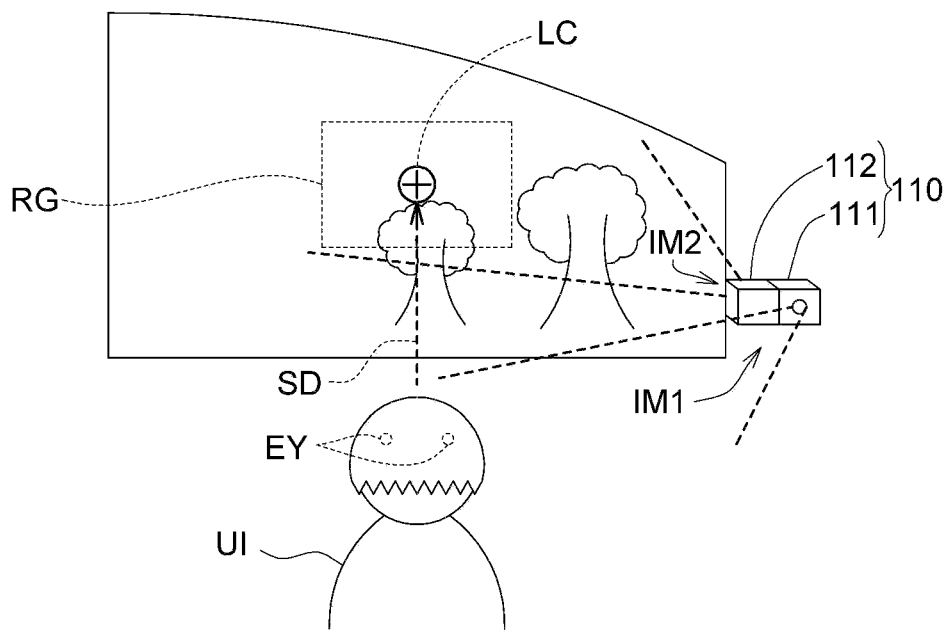
FIG. 7 illustrates the steps in FIG. 6.

Please refer to FIGS. 6 to 7. FIG. 6 shows the detailed flowchart of the step S110, and FIG. 7 illustrates the steps in FIG. 6. The step S110 includes steps S111 to S114. At the step S111, as shown in FIG. 4 and FIG. 7, the internal image capturing element 111 of the range extracting unit 110 captures the vehicle interior image IM1 toward the inside of the vehicle. As shown in FIG. 7, the internal image capturing element 111 of the range extracting unit 110 faces the inside of the vehicle; the external image capturing element 112 of the range extracting unit 110 faces the outside of the vehicle. The internal image capturing element 111 facing the inside of the vehicle can capture the vehicle interior image IM1.

Then, in the step S112, as shown in FIG. 4 and FIG. 7, the external image capturing element 112 captures the vehicle external image IM2 toward the outside of the vehicle. The external image capturing element 112 facing the outside of the vehicle can capture the vehicle external image IM2.

Then, in the step S113, as shown in FIG. 4 and FIG. 7, after the sight analyzing element 113 obtains the vehicle interior image IM1, the line-of-sight SD of the user U1 is obtained according to the eyes EY of the user U1.

Next, in the step S114, as shown in FIG. 4 and FIG. 7, the range analyzing element 114 obtains the gaze background range RG in the vehicle external image IM2 according to the line-of-sight SD. The gaze background range RG is a range expanding outward for a predetermined distance from the location LC of the line-of-sight SD in the vehicle external image IM2.

Then, in the step S120 of FIG. 5, as shown in FIG. 4, the information analyzing unit 120 obtains a background hue information HUb, a background lightness information LTb, a background brightness information BTb or a road information RD of the gaze background range RG. For example, the hue analyzing element 121 of the information analyzing unit 120 analyzes the average hue of all pixels in the gaze background range RG to obtain the background hue information HUb. The lightness analyzing element 122 of the information analyzing unit 120 analyzes the average lightness (value) of all pixels in the gaze background range RG to obtain the background lightness information LTb. The brightness analyzing element 123 of the information analyzing unit 120 analyzes the average brightness of all pixels in the gaze background range RG to obtain the background brightness information BTb. The vehicle analyzing element 124 of the information analyzing unit 120 analyzes the blur degree in the gaze background range RG, or the moving direction or moving speed variation of the vehicle, etc., to obtain the road information RD.

Figure 8:
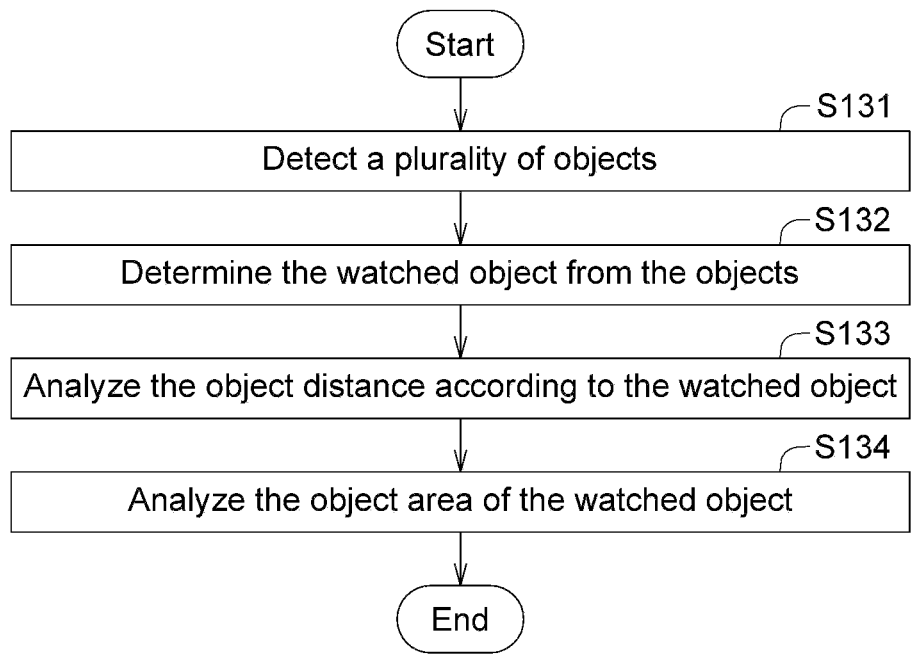
FIG. 8 shows a detailed flowchart of step S130 according to an embodiment.
Figure 9:
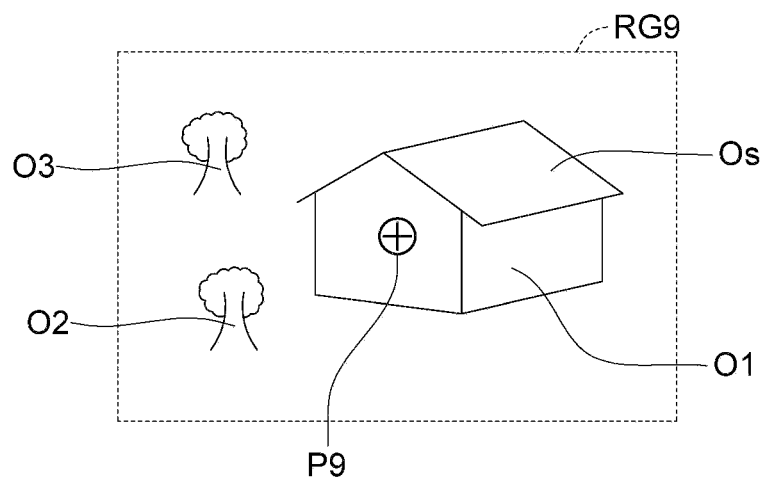
FIG. 9 illustrates the steps in FIG. 8.

Next, in step S130 in FIG. 5, as shown in FIG. 4, the object analyzing unit 130 obtains an object distance Od or an object area Oa of a watched object Os within the gaze background range RG. Please refer to FIGS. 8 to 9. FIG. 8 shows a detailed flowchart of step S130 according to an embodiment, and FIG. 9 illustrates the steps in FIG. 8. In the step S131, as shown in FIG. 4 and FIG. 9, the object identifying element 131 of the object analyzing unit 130, for example, detects a plurality of objects O1, O2, O3 via the semantic segmentation technology.

Then, in the step S132, as shown in FIG. 4 and FIG. 9, the object identifying element 131 of the object analyzing unit 130 determines the watched object Os from the objects O1, O2, and O3. For example, the object identifying element 131 determines the object O1 which is the largest in the gaze background range RG9 as the watched object Os. Or, the object identifying element 131, for example, determines the object O1 overlapping a center point P9 as the watched object Os.

Next, in the step S133, as shown in FIG. 4 and FIG. 9, the distance analyzing element 132 of the object analyzing unit 130 analyzes the object distance Od according to the watched object Os. For example, the distance analyzing element 132 may estimate the object distance Od according to a focal length of the watched object Os.

Next, in the step S134, as shown in FIG. 4 and FIG. 9, the area analyzing element 133 of the object analyzing unit 130 analyzes the object area Oa of the watched object Os.

Then, in step S140 of FIG. 5, as shown in FIG. 4, the image setting unit 140 sets the image hue HU4', the image lightness LT4', the image brightness BT4', the image content CT4' or the ambient lighting display content LB4' of the anti-dizziness reference image PT4' according to the background hue information HUb, the background lightness information LTb, the background brightness information BTb or the road information RD of the gaze background range RG.

Figure 10:
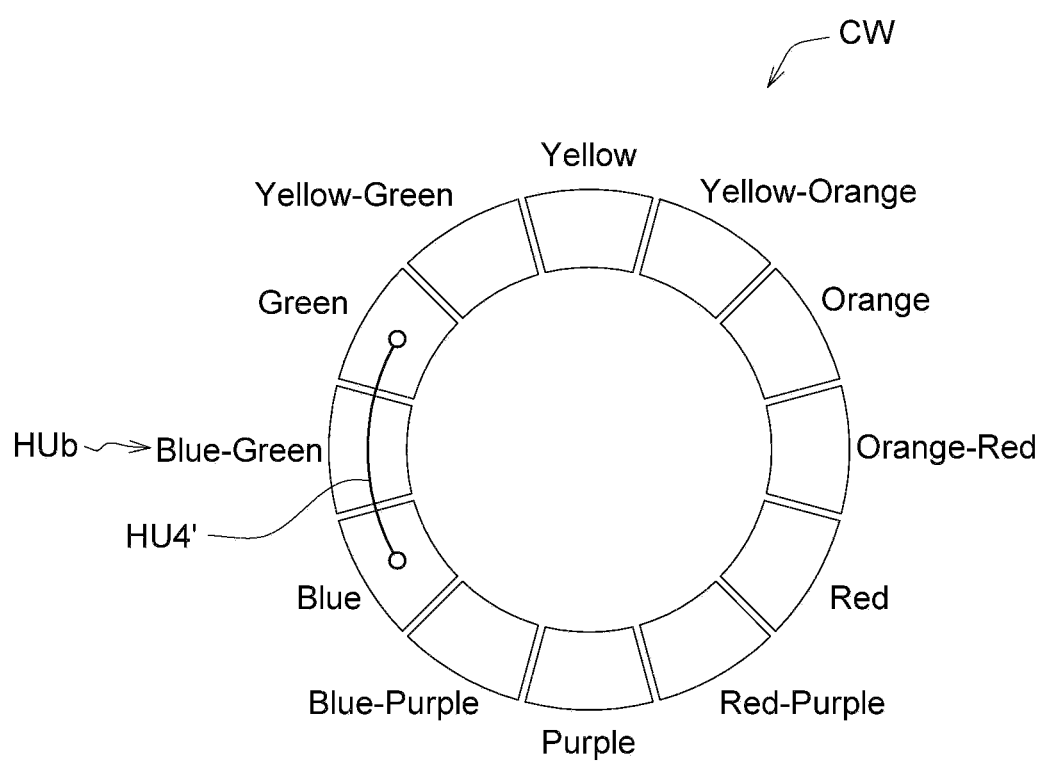
FIG. 10 illustrates how to set the image hue.

In detail, please refer to FIG. 4 and FIG. 10. FIG. 10 illustrates how to set the image hue HU4'. The hue setting element 141 of the image setting unit 140 performs the setting based on the background hue information Hub. For example, the image hue HU4' is set within a range of 30 to 60 degrees in a positive direction or a negative direction of a color wheel CW. Taking the 30 degrees as an example, when the background hue information HUb is "Blue-Green", the image hue HU4' can be set to "Blue", "Blue-Green" or "Green". The image hue HU4' is set according to this way, so that the change between the background hue information HUb and the image hue HU4' would not be too large, so as to avoid excessive eye-catching of the anti-dizziness reference image PT4'.

Figure 11:
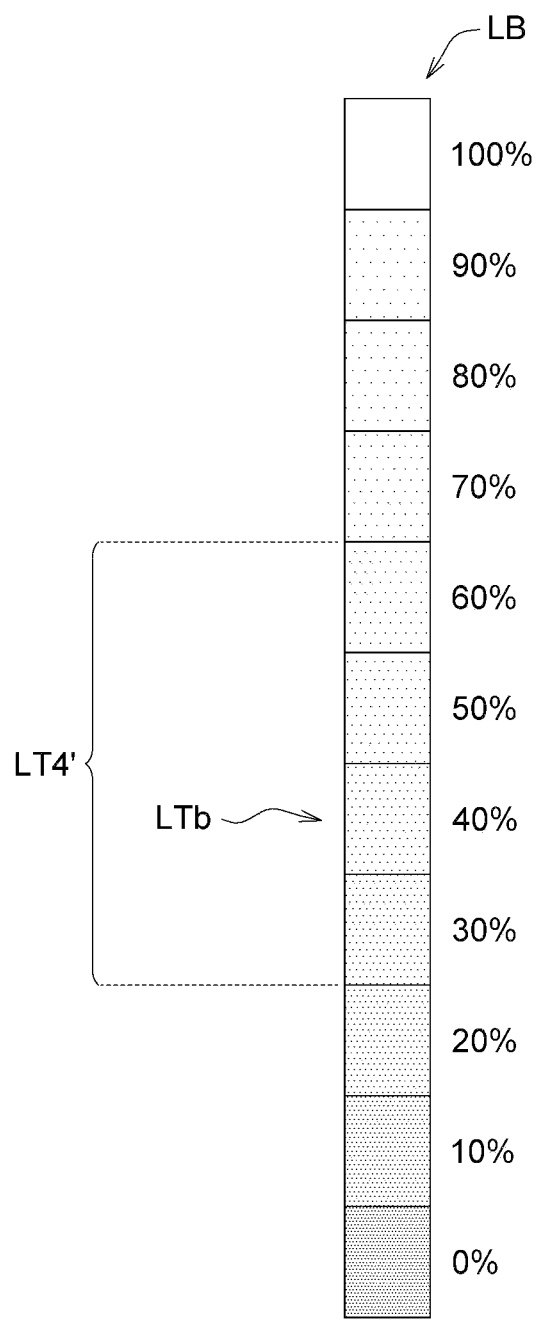
FIG. 11 illustrates how to set the image lightness.

Please refer to FIG. 4 and FIG. 11. FIG. 11 illustrates how to set the image lightness LT4'. In FIG. 11, the lightness bar LB shows the lightness (value) from 0% to 100%. The anti-dizziness reference image PT4', for example, consists of several dots. The lightness (value) represents the density of the dots. There are almost no dot at 0% lightness, and the anti-dizziness reference image PT4' cannot be seen on the transparent display unit at all; the higher the lightness (value), the higher the density of dots, and the clearer the anti-dizziness reference image PT4' can be seen on the transparent display unit. The lightness setting element 142 of the image setting unit 140 sets the image lightness LT4' in the range of 10% to 40% in a positive direction or a reverse direction of the lightness (value) bar LB according to the background lightness information LTb, and the image lightness LT4' is set to be more than 20%. For example, taking the range of 20% as an example, when the background lightness information LTb is "40%", the image lightness LT4' is set to be "60%", "50%", "40%", "30%." By setting the image lightness LT4' in the above way, the difference between the background lightness information LTb and the image lightness LT4' will not be too large, so as to avoid excessive eye-catching of the anti-dizziness reference image PT4'.

In addition, if the background brightness information BTb is less than a maximum brightness provided by the display unit 160 (for example, 400 nits), the brightness setting element 143 may set the image brightness BT4', for example, within a range of the external brightness of the vehicle and the internal brightness of the vehicle. The image brightness BT4' is set within the range of the external brightness of the vehicle and the internal brightness of the vehicle, so that the user can see the anti-dizziness reference image PT4', but it will not be too dazzling.

If the background brightness information BTb is greater than or equal to the maximum brightness provided by the display unit 160 (e.g., 400 nits), then the brightness setting element 143 sets the image brightness BT4' to be the maximum brightness (e.g., 400 nits). When the background brightness information BTb is too large, the anti-dizziness reference image PT4' is maximized as much as possible, so that the user can see the anti-dizziness reference image PT4'.

Furthermore, if the road information RD shows that the vehicle will be shaken much, the graphic setting element 144 may set the image content CT4' to be a simplified pattern, so that the user can easily see the anti-dizziness reference image PT4'.

Or, the road information RD is, for example, the change of the moving direction or the moving speed of the vehicle. The light setting element 146 sets the ambient lighting display content LB4' according to the moving direction or the moving speed of the vehicle. The ambient lighting display content LB4' is, for example, the display color, the display position, the change direction or the color proportion. The following are some examples.

Figure 12A:
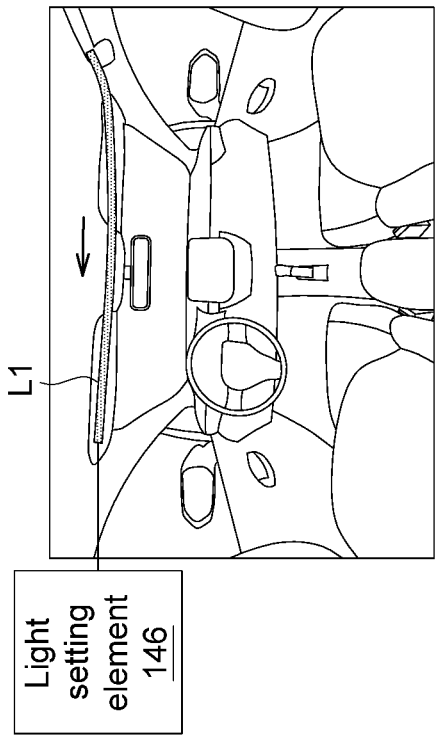
FIGS. 12A to 12D illustrate the ambient lighting display content according to some embodiments.
Figure 12B:
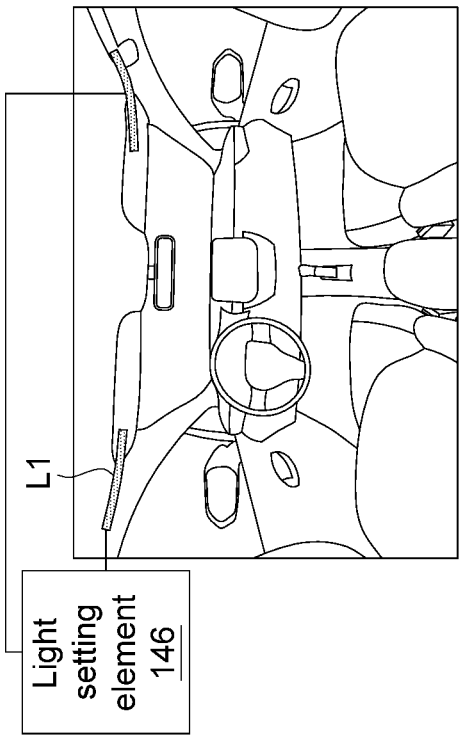
Figure 12C:
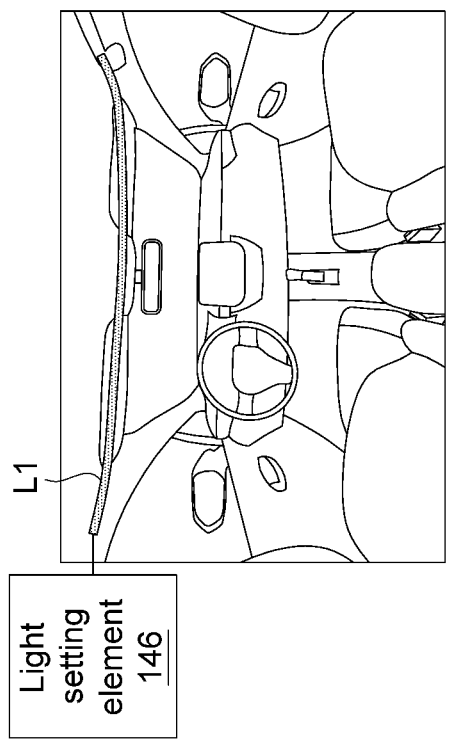
Figure 12D:
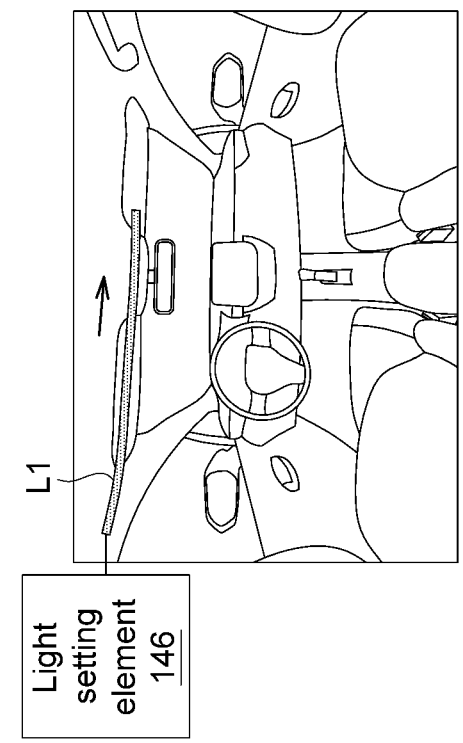

Please refer to FIGS. 12A to 12D, which illustrate the ambient lighting display content LB4' according to some embodiments. In FIG. 12A, when the vehicle is moving forward, the light setting element 146, for example, sets a front window ambient light L1 to display a full-bright light bar. In FIG. 12B, when the vehicle is turning left, the light setting element 146, for example, sets the front window ambient light L1 to display a light bar moving to the left. In FIG. 12C, when the vehicle is turning right, the light setting element 146, for example, sets the front window ambient light L1 to display a light bar moving to the right. In FIG. 12D, the vehicle is stopping, and the light setting element 146, for example, sets the front window ambient light L1 to display short light bars on both sides. The above are examples only, and the present disclosure is not limited thereto.

Figure 13A:
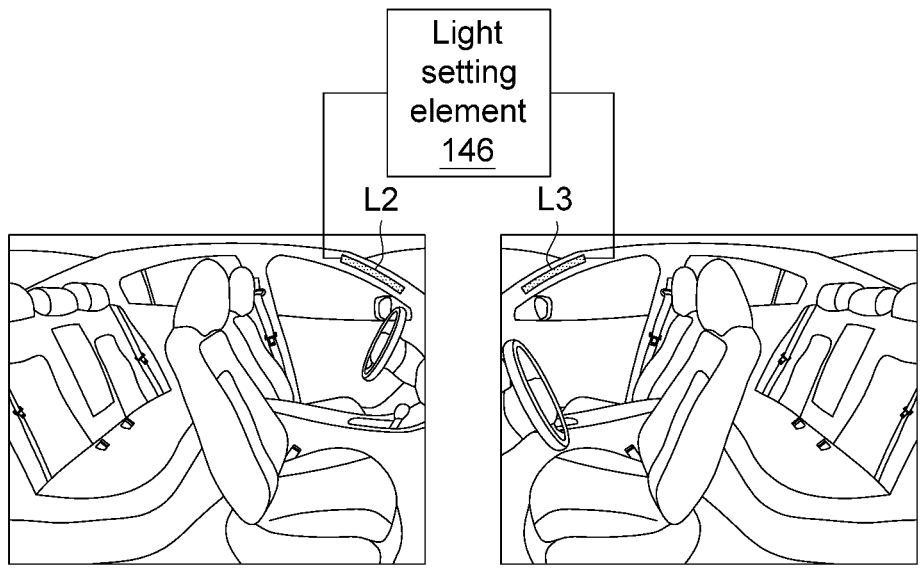
FIG. 13A to 13D illustrate the ambient lighting display content according to some embodiments.
Figure 13B:
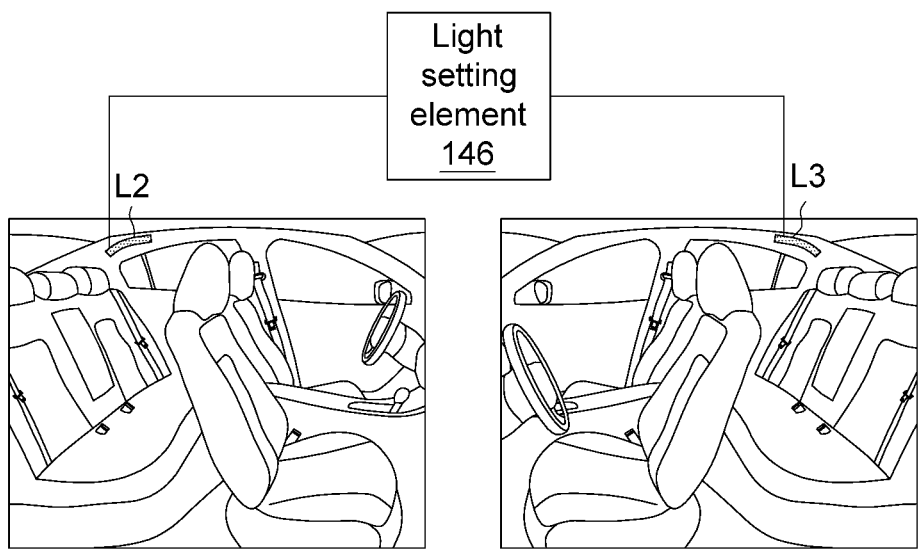
Figure 13C:
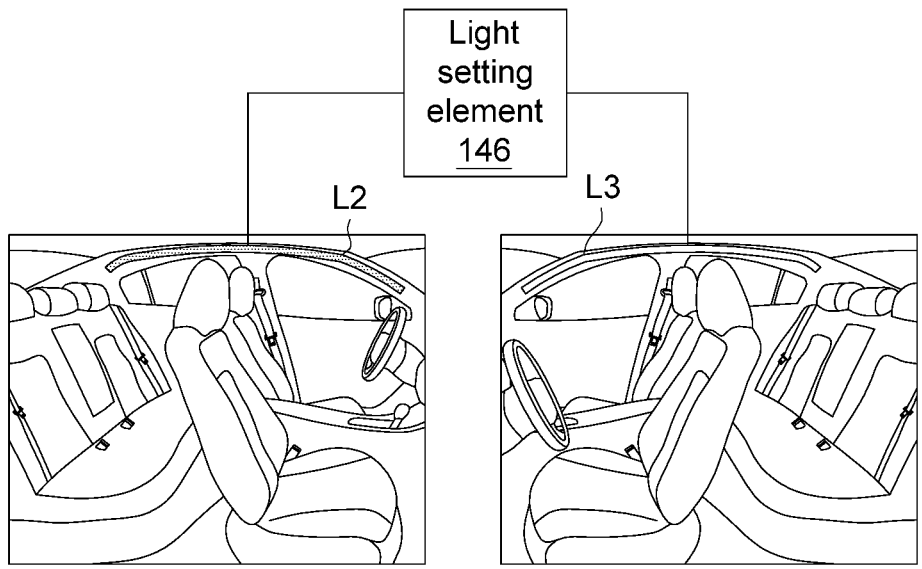
Figure 13D:
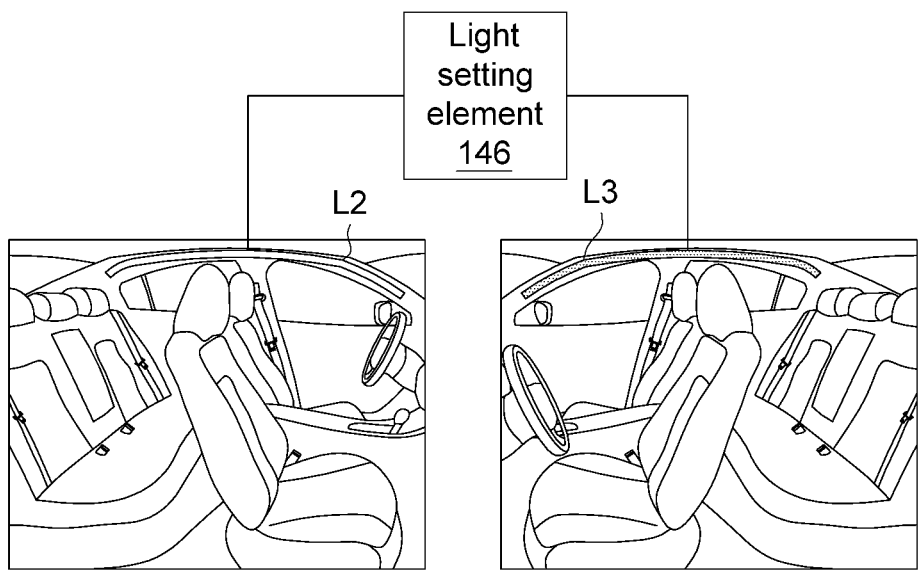

Please refer to FIG. 13A to 13D, which illustrate the ambient lighting display content LB4' according to some embodiments. In FIG. 13A, when the vehicle is moving forward, the light setting element 146, for example, sets a left window ambient light L2 and a right window ambient light L3 to display short light bars ahead. In FIG. 13B, when the vehicle is stopping, and the light setting element 146, for example, sets the left window ambient light L2 and the right window ambient light L3 to display the rear short light bar. In FIG. 13C, when the vehicle is turning left, the light setting element 146, for example, sets the left window ambient light L2 to display a long light bar, and turns off the right window ambient light L3. In FIG. 13D, when the vehicle is turning right, the light setting element 146, for example, sets the right window ambient light L3 to display a long light bar, and turns off the left window ambient light L2. The above are examples only, and the present disclosure is not limited thereto.

Figure 14A:
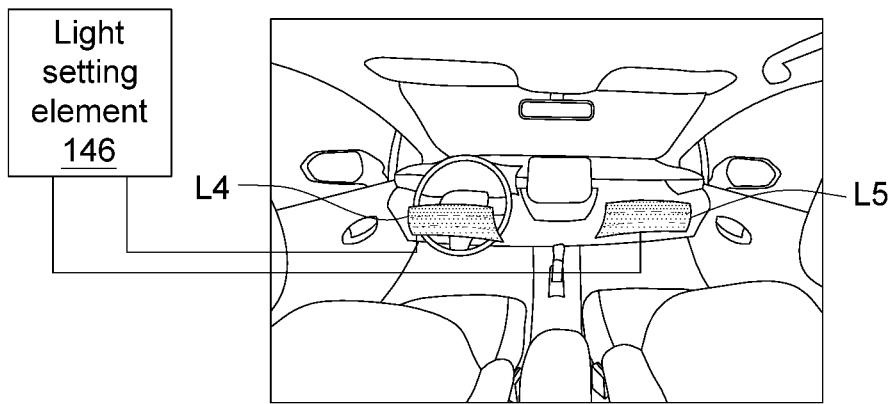
FIGS. 14A to 14C illustrate the ambient lighting display content according to some embodiments.
Figure 14B:
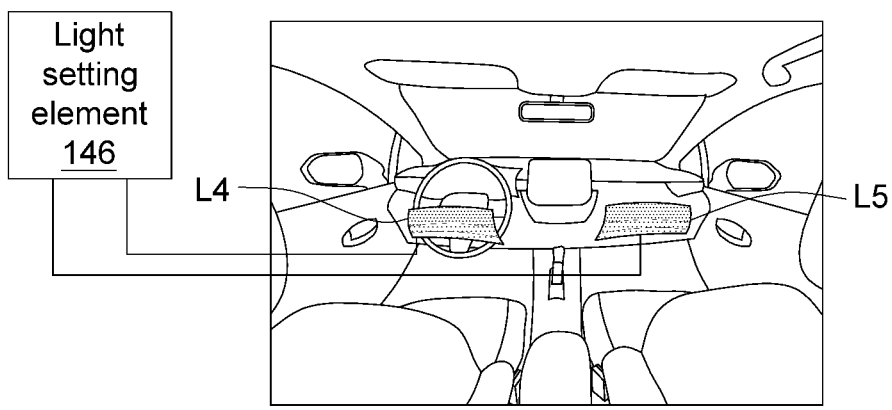
Figure 14C:
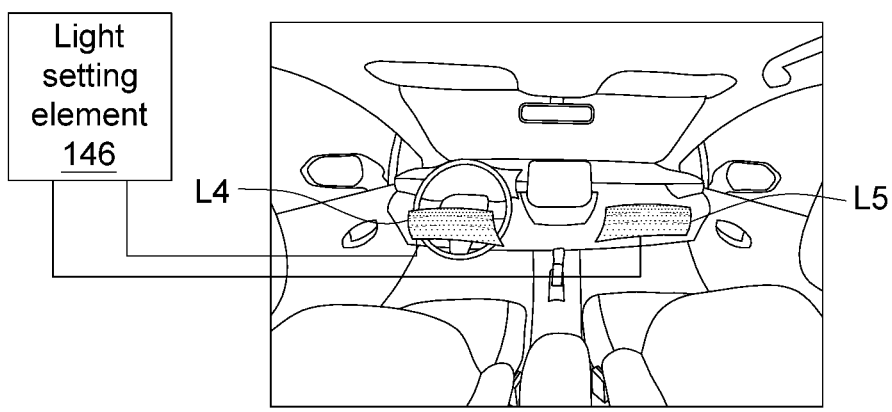

Please refer to FIGS. 14A to 14C, which illustrate the ambient lighting display content LB4' according to some embodiments. In FIG. 14A, when the vehicle is in a horizontal state, the light setting element 146, for example, sets a driver's seat ambient light L4 and a passenger's seat ambient light L5 to display a gradient pattern with the first color and the second color. The top of the gradient pattern is mixed 100% of the first color and 0% of the second color. From the top of the gradient pattern to the bottom of the gradient pattern, the proportion of the first color is gradually reduced every other interval, and the second color is gradually increased every other interval. The bottom of the gradient pattern is mixed 0% of the first color and 100% of the second color. The intervals are substantially the same, and the proportion of the first color and the proportion of the second color are changed in a symmetrical way up and down.

In FIG. 14B, when the vehicle is climbing, the light setting element 146, for example, sets the driver's seat ambient light L4 and the passenger's seat ambient light L5 to display the gradient pattern with the first color and the second color. The top of the gradient pattern is mixed 100% of the first color and 0% of the second color. From the top of the gradient pattern to the bottom of the gradient pattern, the proportion of the first color is gradually reduced every other interval, and the second color is gradually increased every other interval. The bottom of the gradient pattern is mixed 0% of the first color and 100% of the second color. The intervals is changed from large to small from top to bottom, so that the first color with a high proportion occupies a larger range at the top.

In FIG. 14C, when the vehicle is going downhill, the light setting element 146, for example, sets the driver's seat ambient light L4 and the passenger's seat ambient light L5 to display the gradient pattern with the first color and the second color. The top of the gradient pattern is mixed 100% of the first color and 0% of the second color. From the top of the gradient pattern to the bottom of the gradient pattern, the proportion of the first color is gradually reduced every other interval, and the second color is gradually increased every other interval. The bottom of the gradient pattern is mixed 0% of the first color and 100% of the second color. The intervals is changed from small to large from top to bottom, so that the second color with a high proportion occupies a larger range at the bottom. The above are examples only, and the present disclosure is not limited thereto.

Figure 15A:
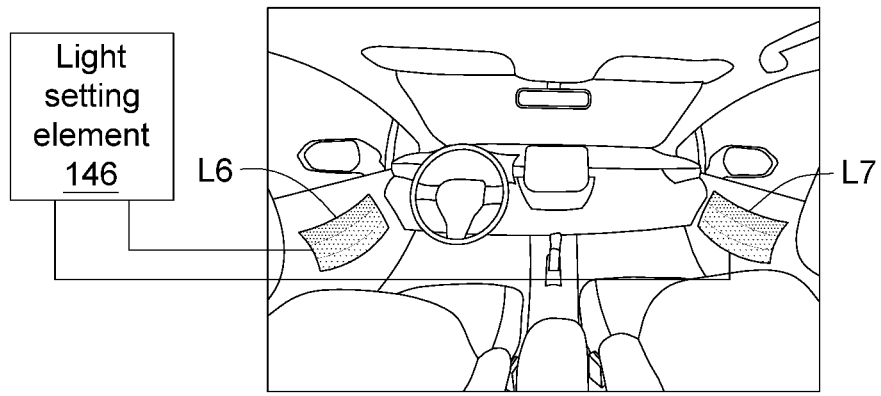
FIGS. 15A to 15C illustrate the ambient lighting display content according to some embodiments.
Figure 15B:
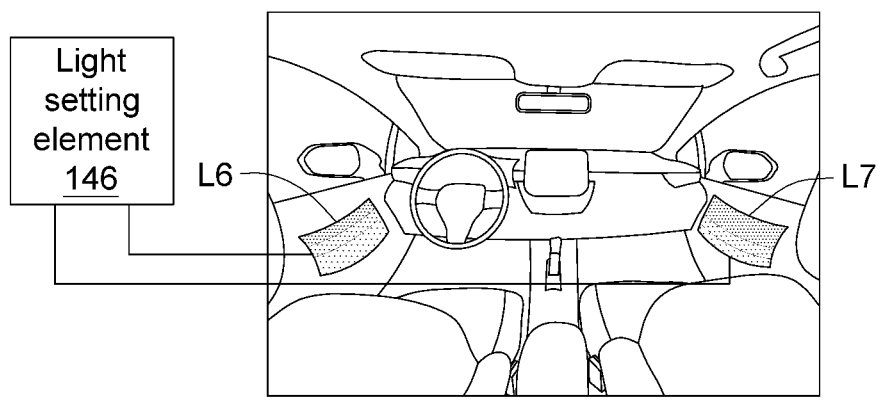
Figure 15C:
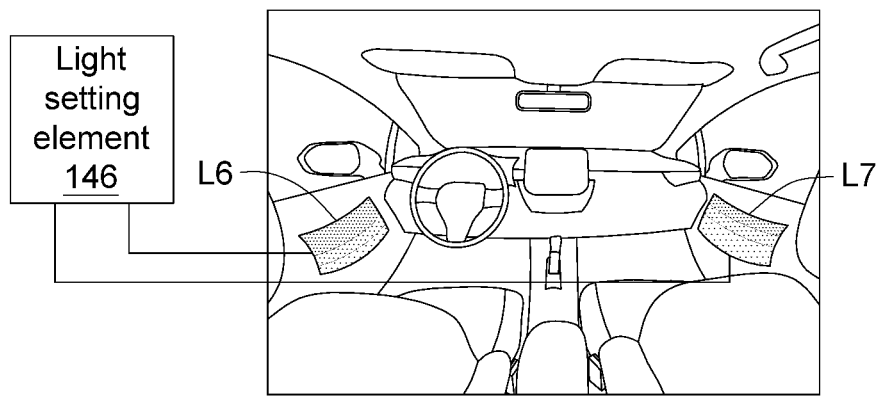

Please refer to FIGS. 15A to 15C, which illustrate the ambient lighting display content LB4' according to some embodiments. In FIG. 15A, when the vehicle is in a horizontal state, the light setting element 146, for example, sets a driver's door ambient light L6 and a passenger's door panel ambient light L7 to display the gradient pattern with the first color and the second color. The top of the gradient pattern is mixed 100% of the first color and 0% of the second color. From the top of the gradient pattern to the bottom of the gradient pattern, the proportion of the first color is gradually reduced every other interval, and the second color is gradually increased every other interval. The bottom of the gradient pattern is mixed 0% of the first color and 100% of the second color. The intervals are substantially the same, and the proportion of the first color and the proportion of the second color are changed in a symmetrical way up and down.

In FIG. 15B, when the vehicle is leaning to the left, the light setting element 146, for example, sets the driver's door ambient light L6 and the passenger's door panel ambient light L7 to display the gradient pattern with the first color and the second color. In the driver's door ambient light L6, the top of the gradient pattern is mixed 100% of the first color and 0% of the second color. From the top of the gradient pattern to the bottom of the gradient pattern, the proportion of the first color is gradually reduced every other interval, and the second color is gradually increased every other interval. The bottom of the gradient pattern is mixed 0% of the first color and 100% of the second color. The intervals is changed from small to large from top to bottom, so that the second color with a high proportion occupies a larger range at the bottom of the gradient pattern. In the passenger's door panel ambient light L7, the top of the gradient pattern is mixed 100% of the first color and 0% of the second color. From the top of the gradient pattern to the bottom of the gradient pattern, the proportion of the first color is gradually reduced every other interval, and the second color is gradually increased every other interval. The bottom of the gradient pattern is mixed 0% of the first color and 100% of the second color. The intervals is changed from large to small from top to bottom, so that the first color with a high proportion occupies a larger range at the top.

In FIG. 15C, when the vehicle is leaning right, the light setting element 146, for example, sets the driver's door ambient light L6 and the passenger's door panel ambient light L7 to display the gradient pattern with the first color and the second color. In the driver's door ambient light L6, the top of the gradient pattern is mixed 100% of the first color and 0% of the second color. From the top of the gradient pattern to the bottom of the gradient pattern, the proportion of the first color is gradually reduced every other interval, and the second color is gradually increased every other interval. The bottom of the gradient pattern is mixed 0% of the first color and 100% of the second color. The intervals is changed from large to small from top to bottom, so that the first color with a high proportion occupies a larger range at the top. In the passenger's door panel ambient light L7, the top of the gradient pattern is mixed 100% of the first color and 0% of the second color. From the top of the gradient pattern to the bottom of the gradient pattern, the proportion of the first color is gradually reduced every other interval, and the second color is gradually increased every other interval. The bottom of the gradient pattern is mixed 0% of the first color and 100% of the second color. The intervals is changed from small to large from top to bottom, so that the second color with a high proportion occupies a larger range at the bottom.

Next, in the step S140' in FIG. 5, as shown in FIG. 4, the scale setting element 145 of the image setting unit 140 sets an image proportion RT4' of the anti-dizziness reference image PT4' to the display area Da of the display unit 160 according to the object distance Od or the object area Oa of the watched object Os.

In one embodiment, the scale setting element 145 obtains the image proportion RT4' according to the following formula (1), for example.

$$\text{if } Rsw \geq 0.5, RT4' \leq 0.5$$

$$\text{if } Rsw < 0.5, RT4' \leq Rsw \qquad (1)$$

According to formula (1), if the scenery proportion Rsw of the object area Oa to the Field Of View (FOV) area Fa of the external image capturing element 112 is greater than or equal to 0.5, the scale setting element 145 sets the image proportion RT4' to be below 0.5. If the scenery proportion Rsw of the object area Oa to the FOV area Fa is less than 0.5, the scale setting element 145 sets the image proportion RT4' to be below the scenery proportion Rsw. Through the setting of the image proportion RT4', the anti-dizziness reference image PT4' will not be too large, so that the user's viewing of the watched object Os will not be affected, or the watched object Os would not be blocked.

In addition, in another embodiment, the scale setting element 145 obtains the image proportion RT4' according to the following formula (2), for example.

$$\text{if } Od < Vd, RT4' = \left(\frac{Vd - Od}{Vd}\right) * 0.5 \qquad (2)$$

$$\text{if } Od \geq Vd, RT4' = 0.0001$$

According to the formula (2), the image proportion RT4' is the output of the function of the user's furthest viewing distance Vd and object distance Od. The scale setting element 145 sets the image proportion RT4' being negatively related to the object distance Od. In addition, the scale setting element 145 sets the lower limit of the image proportion RT4' to be 0.001.

Figure 16:
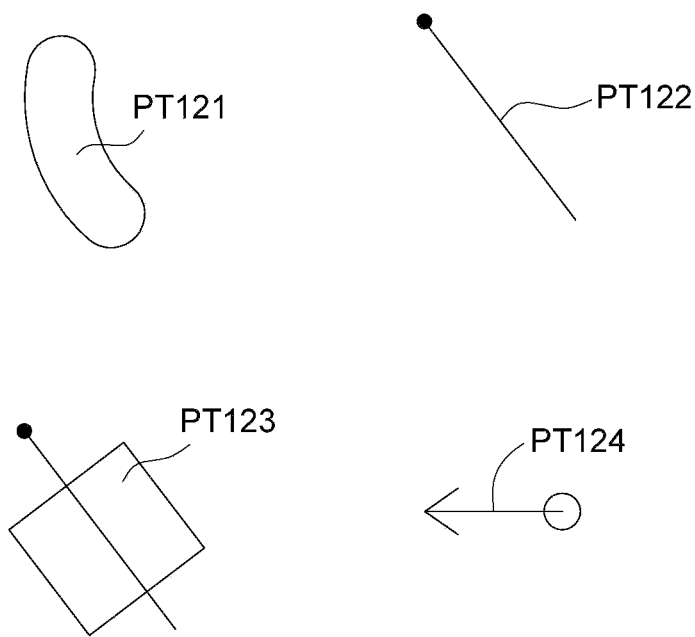
FIG. 16 illustrates the number of lines of different anti-dizziness reference images.

Next, in the step S150 of FIG. 5, the image base condition setting unit 150 sets a basic condition of the anti-dizziness reference image PT4'. For example, as shown in FIG. 4, the shape setting element 151 of the image base condition setting unit 150 sets the number of lines NM4' of the anti-dizziness reference image PT4' to be less than 25. Please refer to FIG. 16, which illustrates the number of lines of different anti-dizziness reference images PT121, PT122, PT123, PT124. The number of lines is recorded by counting any line whose ends are not connected to any other line, and by counting any surface whose edges are connected. For example, the number of lines of the anti-dizziness reference image PT121 is 1; the number of lines of the anti-dizziness reference image PT122 is 1; the number of lines of the anti-dizziness reference image PT123 is 2; the number of lines of the anti-dizziness reference image PT124 is 3. In this embodiment, the number of lines NM4' of the anti-dizziness reference image PT4' is set to be less than 25, so that the anti-dizziness reference image PT4' is prevented from being too complicated and the burden on the human eye can be reduced.

In addition, as shown in FIG. 4, the color setting element 152 of the image base condition setting unit 150, for example, sets the image saturation CL4' of the anti-dizziness reference image PT4' between 0% and 70%, so that the anti-dizziness reference image PT4' is avoided being too eye-catching and the burden on the human eye would be reduced.

Furthermore, as shown in FIG. 4, the transparency setting element 153 of the image base condition setting unit 150, for example, sets the image transparency TP4' of the anti-dizziness reference image PT4' between 30% to 70%, so that the anti-dizziness reference image PT4' would not block the background and the visual interference to the user would be reduced.

Then, in the step S160 in FIG. 5, the anti-dizziness reference image PT4' is display by the display unit 160. After the above settings on the anti-dizziness reference image PT4', the anti-dizziness reference image PT4' would not being too eye-catching, the anti-dizziness reference image PT4' would not block the scenery outside the window, the anti-dizziness reference image PT4' would not interfere with the user's vision, and improve of the visual comfort would be improved.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A display method for an anti-dizziness reference image, comprising:
    obtaining a gaze background range of a user;
    obtaining a background hue information, a background lightness information, a background brightness information or a road information of the gaze background range;
    obtaining an object distance or an object area of a watched object in the gaze background range;
    setting an image hue, an image lightness, an image brightness, an image content or an ambient lighting display content of the anti-dizziness reference image according to the background hue information, the background lightness information, the background brightness information or the road information of the gaze background range; or setting an image proportion of the anti-dizziness reference image to a display area of the display unit according to the object distance or the object area of the watched object, wherein the anti-dizziness reference image is used to balance the user's vision and vestibular perception to avoid a dizziness of the user; and
    displaying, by a display unit, the anti-dizziness reference image.

2. The display method for the anti-dizziness reference image according to claim 1, wherein
    the step of setting the image hue, the image lightness, the image brightness, the image content or the ambient lighting display content of the anti-dizziness reference image includes setting the image hue within the range of 30 to 60 degrees in a positive direction or in a reverse direction of a color wheel according to the background hue information;
    or the step of setting the image hue, the image lightness, the image brightness, the image content or the ambient lighting display content of the anti-dizziness reference image includes setting the image lightness within a range of 10% to 40% in a positive direction or a negative direction of a lightness bar, and setting the image lightness to be greater than 20% according to the background lightness information;
    or the step of setting the image hue, the image lightness, the image brightness, the image content or the ambient lighting display content of the anti-dizziness reference image includes setting the image brightness within a range of a vehicle external brightness to a vehicle internal brightness if the background brightness information is less than a maximum brightness provided by the display unit;
    or the step of setting the image hue, the image lightness, the image brightness, the image content or the ambient lighting display content of the anti-dizziness reference image includes setting the image brightness to be the maximum brightness if the background brightness information is greater than or equal to the maximum brightness provided by the display unit.

3. The display method for the anti-dizziness reference image according to claim 1, further comprising:
    setting number of lines of the anti-dizziness reference image to be less than 25.

4. The display method for the anti-dizziness reference image according to claim 1, further comprising:
    setting an image saturation of the anti-dizziness reference images to be within a range of 0% to 70%.

5. The display method for the anti-dizziness reference image according to claim 1, further comprising:
    setting an image transparency of the anti-dizziness reference image within a range of 30% to 70%.

6. The display method for the anti-dizziness reference image according to claim 1, wherein in the step of setting the image proportion of the anti-dizziness reference image to the display area of the display unit,
    if a scenery proportion of the object area to a Field Of View (FOV) area is greater than or equal to 0.5, then the image proportion is set to be below 0.5;
    if the scenery proportion of the object area to the FOV area is less than 0.5, then the image proportion is set to be below the scenery proportion.

7. The display method for the anti-dizziness reference image according to claim 1, wherein in the step of setting the image proportion of the anti-dizziness reference image to the display area of the display unit, the image proportion is set to be negatively related to the object distance, and a lower limit of the image proportion is set to be 0.001.

8. The display method for the anti-dizziness reference image according to claim 1, wherein the road information is a moving direction or a moving speed variation.

9. The display method for the anti-dizziness reference image according to claim 1, wherein the ambient lighting display content is a display color, a display position, a change direction, or a color mixing ratio.

10. A display system for an anti-dizziness reference image, wherein the display system is used to:

display the anti-dizziness reference image, wherein the anti-dizziness reference image is used to balance the user's vision and vestibular perception to avoid a dizziness of the user;

obtain a gaze background range of a user;

obtain a background hue information, a background lightness information, a background brightness information or a road information of the gaze background range;

obtain an object distance or an object area of a watched object in the gaze background range; and set an image hue, an image lightness, an image brightness, an image content or an ambient lighting display content of the anti-dizziness reference image according to the background hue information, the background lightness information, the background brightness information or the road information of the gaze background range; or set an image proportion of the anti-dizziness reference image to a display area according to the object distance or the object area of the watched object.

11. The display system for the anti-dizziness reference image according to claim 10, wherein the display system is further used to set the image hue within the range of 30 to 60 degrees in a positive direction or in a reverse direction of a color wheel according to the background hue information.

12. The display system for the anti-dizziness reference image according to claim 10, wherein the display system is further used to set the image lightness within a range of 10% to 40% in a positive direction or a negative direction of a lightness bar, and set the image lightness to be greater than 20% according to the background lightness information.

13. The display system for the anti-dizziness reference image according to claim 10, wherein the display system is further used to set the image brightness within a range of a vehicle external brightness to a vehicle internal brightness, if the background brightness information is less than a maximum brightness; and the display system is further used to set the image brightness to be the maximum brightness, if the background brightness information is greater than or equal to the maximum brightness.

14. The display system for the anti-dizziness reference image according to claim 10, wherein the display system is further used to set number of lines of the anti-dizziness reference image to be less than 25.

15. The display system for the anti-dizziness reference image according to claim 10, wherein the display system is further used to set an image saturation of the anti-dizziness reference images to be within a range of 0% to 70%.

16. The display system for the anti-dizziness reference image according to claim 10, wherein the display system is further used to set an image transparency of the anti-dizziness reference image within a range of 30% to 70%.

17. The display system for the anti-dizziness reference image according to claim 10, wherein the display system is further used to set the image proportion to be below 0.5, if a scenery proportion of the object area to a Field Of View (FOV) area is greater than or equal to 0.5; and the display system is further used to set the image proportion to be below the scenery proportion, if the scenery proportion of the object area to the FOV area is less than 0.5.

18. The display system for the anti-dizziness reference image according to claim 10, wherein the display system is further used to set the image proportion to be negatively related to the object distance, and set a lower limit of the image proportion to be 0.001.

19. The display system for the anti-dizziness reference image according to claim 10, wherein the road information is a moving direction or a moving speed variation.

20. The display system for the anti-dizziness reference image according to claim 10, wherein the ambient lighting display content is a display color, a display position, a change direction, or a color mixing ratio.

* * * * *